United States Patent
Koshti

(10) Patent No.: US 11,747,287 B1
(45) Date of Patent: Sep. 5, 2023

(54) RADIOGRAPHIC CRACK IMAGE QUALITY INDICATOR SYSTEM AND METHOD

(71) Applicant: United States of America as represented by the Administrator of NASA, Washington, DC (US)

(72) Inventor: Ajay M Koshti, League City, TX (US)

(*) Notice: Subject to any disclaimer, the term of this patent is extended or adjusted under 35 U.S.C. 154(b) by 221 days.

(21) Appl. No.: 17/371,525

(22) Filed: Jul. 9, 2021

Related U.S. Application Data

(60) Provisional application No. 63/094,446, filed on Oct. 21, 2020.

(51) Int. Cl.
| G01N 23/18 | (2018.01) |
| G01N 23/04 | (2018.01) |
| G01N 23/083 | (2018.01) |

(52) U.S. Cl.
CPC .......... *G01N 23/18* (2013.01); *G01N 23/04* (2013.01); *G01N 23/083* (2013.01); *G01N 2223/1016* (2013.01); *G01N 2223/3035* (2013.01); *G01N 2223/401* (2013.01); *G01N 2223/41* (2013.01); *G01N 2223/646* (2013.01); *G01N 2223/6466* (2013.01)

(58) Field of Classification Search
None
See application file for complete search history.

(56) References Cited

U.S. PATENT DOCUMENTS

| 4,055,771 A * | 10/1977 | Goodenough | G21K 1/10 378/207 |
| 4,669,104 A * | 5/1987 | Mangenet | G01N 23/18 378/207 |
| 5,210,783 A * | 5/1993 | Wallace | G01N 23/04 378/207 |
| 5,994,900 A * | 11/1999 | Gurvich | G01R 33/58 324/300 |

(Continued)

FOREIGN PATENT DOCUMENTS

| EP | 0186563 A1 * | 7/1986 | G01N 23/18 |
| JP | 2005031013 A * | 2/2005 | |
| WO | WO-2004020988 A1 * | 3/2004 | A61B 5/1076 |

OTHER PUBLICATIONS

Muzibur Khan et al., "Computer Radiography for High Resolution Imaging Applications of Aircraft Structures", NDT in Aerospace 11th International Symposium.

(Continued)

*Primary Examiner* — Thomas R Artman
(74) *Attorney, Agent, or Firm* — David G. Matthews; Edward K. Fein

(57) ABSTRACT

An image quality indicator (IQI) system includes a crack IQI. The crack IQI includes a penetrameter having a first body and a second body disposed in the first body. The first body has a first body inner surface defining a first body hole. The second body has a second body outer surface disposed adjacent the first body inner surface to form an interface having an interface gap. The IQI system also includes a (Continued)

radiation source spaced from the penetrameter and configured to transmit radiation rays to the penetrameter. The IQI system also includes a radiation detector disposed adjacent the penetrameter and configured to generate an IQI radiographic image indicative of an interface gap characteristic of the interface gap.

20 Claims, 12 Drawing Sheets

(56) References Cited

U.S. PATENT DOCUMENTS

| | | | |
|---|---|---|---|
| 6,658,089 B1 | 12/2003 | Mohr et al. | |
| 7,999,219 B2 | 8/2011 | Skuse et al. | |
| 8,577,120 B1 | 11/2013 | Koshti | |
| 9,720,114 B2 | 8/2017 | Blagojevic et al. | |
| 9,787,913 B1 | 10/2017 | Koshti | |
| 10,545,100 B2 | 1/2020 | Buijsse et al. | |
| 10,620,133 B1 | 4/2020 | Koshti | |
| 2004/0066188 A1 | 4/2004 | Goldfine et al. | |
| 2009/0161833 A1* | 6/2009 | Skuse | G01N 23/04 378/207 |
| 2011/0266427 A1* | 11/2011 | Blagojevic | G01T 1/169 378/207 |
| 2017/0284947 A1* | 10/2017 | Hutchinson | G01N 23/04 |
| 2020/0232938 A1 | 7/2020 | Fitzgerald et al. | |

OTHER PUBLICATIONS

"Nondestructive Evaluation Requirements for Fracture-Critical Metallic Components",NASA-STD-5009B.
Ajay Koshti, "Simulating the x-ray image contrast to setup tehniques with desired flaw detectability", Proceedings of SPIE vol. 9437.
Ajay Koshti, "X-ray ray tracing simulation and flaw parameters for crack detection", Proceedings of SPIE vol. 10600.
Ajay Koshti, "Assessing Visual and System Flaw Detectability in Nondestructive Evaluation", Proceedings of SPIE vol. 11592, Mar. 2021.
"90/95 POD Radiography Concern for COPVs and Metal Tank Welds", NESC Technical Bulletin No. 19-02.
Ajay Koshti, "Probability of Detection Analysis in Multi-Hit Flaw Detection", SPIE.
I. Elshafiey, "Optimization Tool for X-ray Radiography NDE", Review of Progress in Quantitative Nondestructive Evaluation, vol. 15, 1996.
Ajay Koshti, "Using requirements on merit ratios for assessing reliability of NDE flaw detection", Proceedings of SPIE vol. 11593, Mar. 2021.
Ajay Koshti, "Using requirements on merit ratios for assessing reliability of NDE flaw detection in multi-hit detection in digital radiography", Proceedings of SPIE 11593, Mar. 2021.
Ajay Koshti, "Assessment of flaw detectability using transfer function", Proceedings of SPIE vol. 11592, Mar. 2021.
Ajay Koshti, "Optimizing raster scanning parameters in nondestructive evaluation using simulation of probe sensitivity field", Proceedings of SPIE vol. 11592, Mar. 2021.
Ajay Koshti, "Modeling reliability of NDE method providing C-scan: a case of flaw field simulation", Proceedings of SPIE vol. 11593, Mar. 2021.
Ewert et al, "Minimum Requirements for Digital Radiography Equipment and Measurement Procedures by Different Industries and Standard Organizations".
Muzibur Khan, "Equivalent Penetrameter Sensitivity (EPS) for Performance Evaluation of Computed Radiography Systems".
Ajay Koshti, "Modeling the x-ray process and x-ray flaw size parameter for POD studies", Proceedings of SPIE vol. 9063, Mar. 2014.
Ajay Koshti, "Nondestructive Characterization for Composite Materials, Aerospace Engineering, Civil Infrastructure, and Homeland Security 2014", Proceedings of SPIE vol. 9063.

* cited by examiner

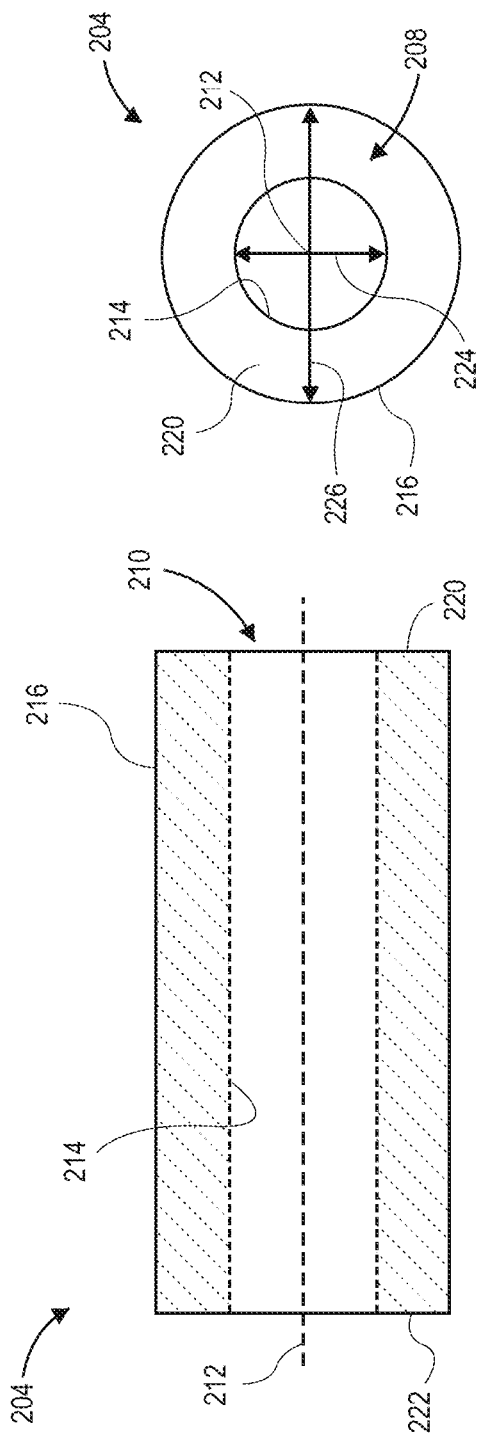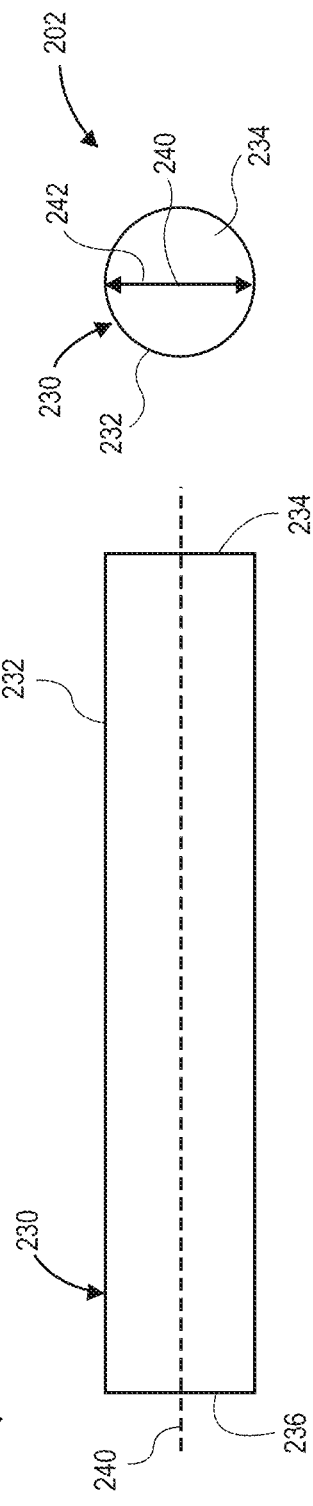

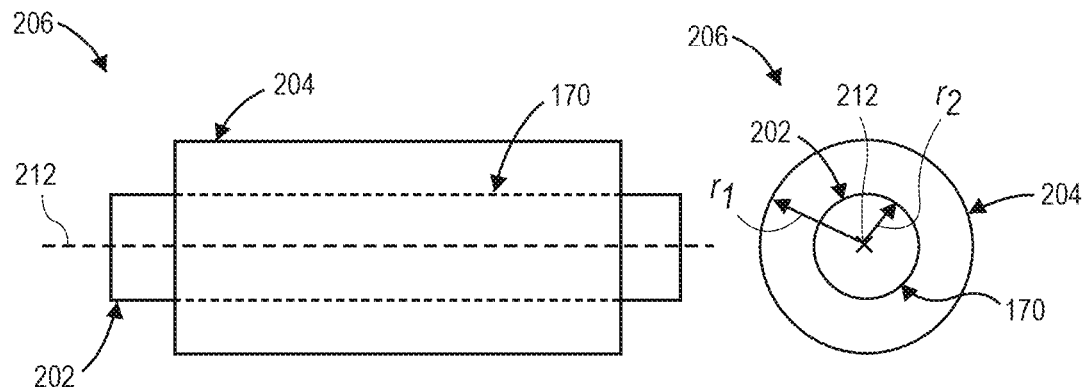
FIG. 19  FIG. 20
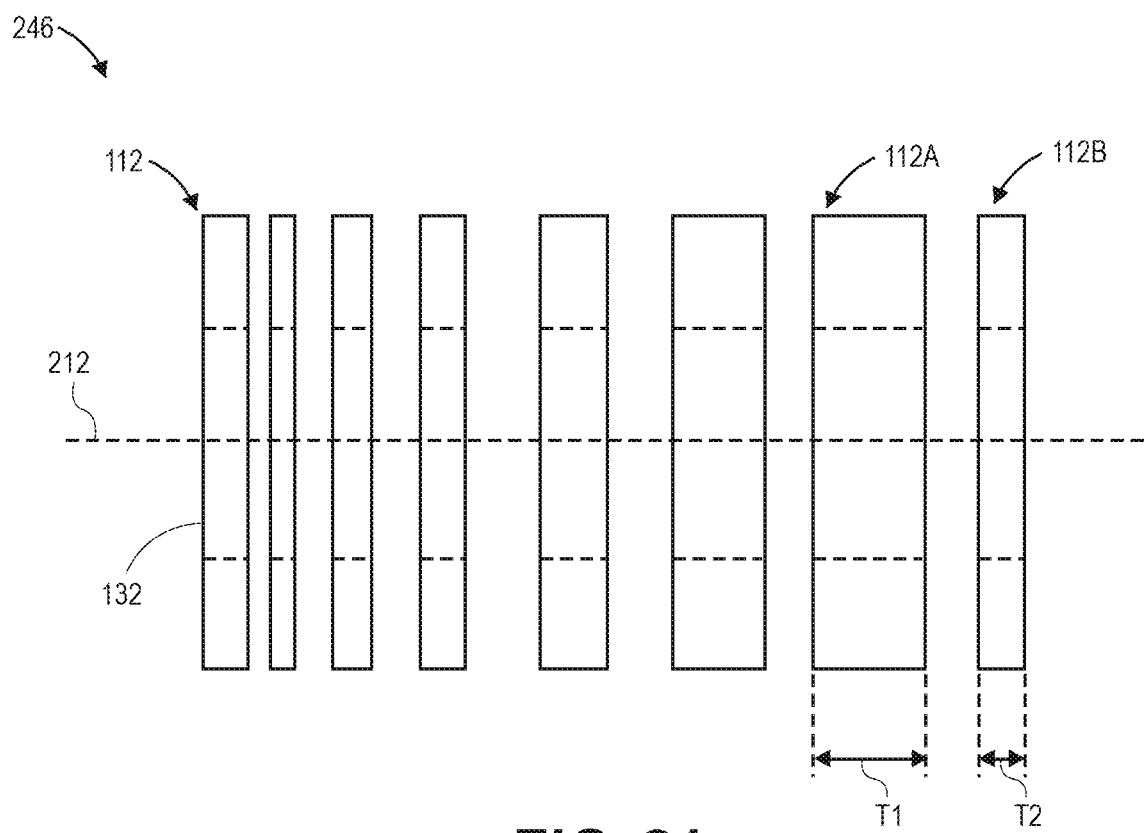
FIG. 21

RADIOGRAPHIC CRACK IMAGE QUALITY INDICATOR SYSTEM AND METHOD

CROSS-REFERENCE TO RELATED APPLICATIONS

This patent application claims priority to U.S. Provisional Patent Application No. 63/094,446, filed on Oct. 21, 2020, the entirety of which is incorporated by reference herein.

BACKGROUND

Radiographic inspection is commonly used to detect cracks a part. The radiographic inspection may include X-ray inspection of the part. The part may be metallic or non-metallic. When the part is metallic, the radiographic inspection may be used to detect cracks in the part or in a weld on the part. Illustrative metal parts may include an aircraft fuselage, aircraft wings, fuel tanks, boilers, fan blades, combustor cases, and other metal parts.

For some parts, radiographic inspection is used to provide reliable detection of cracks that are greater than or equal to a certain minimum size. To provide reliable detection of cracks of a certain minimum size, an image quality indicator (IQI) may be used to determine the sensitivity of the radiographic inspection (i.e., the size(s) of the crack(s) that the radiographic inspection is capable of detecting). The IQI is a device that provides simulated flaws (e.g., a simulated crack) in a part to be inspected. Two kinds of IQIs that have been used in the past include a hole-type IQI and a wire-type IQI. The hole-type IQI and the wire-type IQI typically have been used to detect volumetric flaws of a certain minimum size.

An IQI system with a crack IQI that simulates cracks that may have very little gap between crack faces in a part is needed. In addition, a process for manufacturing a crack IQI is needed.

SUMMARY

The embodiments described herein include systems and methods for a radiographic crack image quality indicator. In one embodiment, an image quality indicator (IQI) system is disclosed. The IQI system includes a crack IQI. The crack IQI includes a penetrameter having a first body and a second body disposed in the first body. The first body has a first body inner surface defining a first body hole. The second body has a second body outer surface disposed adjacent the first body inner surface to form an interface having an interface gap. The IQI system also includes a radiation source spaced from the penetrameter and configured to transmit radiation rays to the penetrameter. The IQI system also includes a radiation detector disposed adjacent the penetrameter and configured to generate an IQI radiographic image indicative of an interface gap characteristic of the interface gap.

A method is also disclosed. The method includes positioning a crack image quality indicator (IQI) adjacent to a radiation detector. The crack IQI includes a penetrameter having a washer and a plug disposed in the washer. The washer has a washer inner surface defining a washer hole. The plug has a plug outer surface disposed adjacent the washer inner surface to form a hole-plug interface having a predetermined interface gap. The method also includes radiographic imaging the penetrameter with a radiation source. The radiographic imaging includes activating the radiation source, and collecting a first radiographic image with the radiation detector.

A method for detecting cracks is also disclosed. The method includes increasing a temperature differential between a shaft and a pipe to allow a frictionless assembly of the shaft into the pipe to form a pipe-shaft assembly. The shaft, the pipe, or both are metallic. The method also includes equalizing temperatures of the shaft and the pipe to form an interference fit between the shaft and the pipe in the pipe-shaft assembly. The method also includes cutting the pipe-shaft assembly into a plurality of sections. Each section serves as at least a portion of a crack image quality indicator (IQI). Each crack IQI includes a washer and that is part of the pipe. The washer has a washer inner surface defining a washer hole. Each crack IQI also includes a plug that is part of the shaft. The plug has a plug outer surface disposed adjacent the washer inner surface to form a hole-plug interface having an interface gap. The method also includes positioning a first of the crack IQIs at least partially between a radiation source and a radiation detector. A central longitudinal axis through the first crack IQI is substantially perpendicular to the radiation detector. The method also includes positioning a shim at least partially between the first crack IQI and the radiation detector. The method also includes performing a qualification test using a qualification system setup. The qualification test includes radiographic imaging the first crack IQI with the radiation source. The radiographic imaging includes activating the radiation source which emits a normal ray and a limit ray. The normal ray is substantially perpendicular to the radiation detector. The limit ray is non-perpendicular to the radiation detector. The normal ray, the limit ray, or both pass through the first crack IQI and are received by the radiation detector. An angle between the normal ray and the limit ray at least partially defines a coverage length on the radiation detector. The radiographic imaging also includes collecting a first radiographic image with the radiation detector in response to receiving the normal ray, the first ray, or both. The method also includes detecting a simulated crack in the first IQI based at least partially upon the first radiographic image. The simulated crack is detected at least partially within the coverage length.

BRIEF DESCRIPTION OF THE DRAWINGS

The following figures form part of the present specification and are included to further demonstrate certain aspects of the presently described subject matter and should not be used to limit it. The present subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings, in which like reference numerals may identify like elements, wherein:

FIG. 15 illustrates a side view of the pipe of the pipe-shaft assembly, according to an embodiment.

FIG. 16 illustrates an end view of the pipe of the pipe-shaft assembly, according to an embodiment.

FIG. 17 illustrates a side view of the shaft of the pipe-shaft assembly, according to an embodiment.

FIG. 18 illustrates an end view of the shaft of the pipe-shaft assembly, according to an embodiment.

FIG. 19 illustrates a side view of the pipe-shaft assembly, according to an embodiment.

FIG. 20 illustrates an end view of the pipe-shaft assembly, according to an embodiment.

FIG. 21 illustrates a schematic view showing the pipe-shaft assembly of FIG. 19 cut into an IQI set, according to an embodiment.

DETAILED DESCRIPTION

Figure 1:
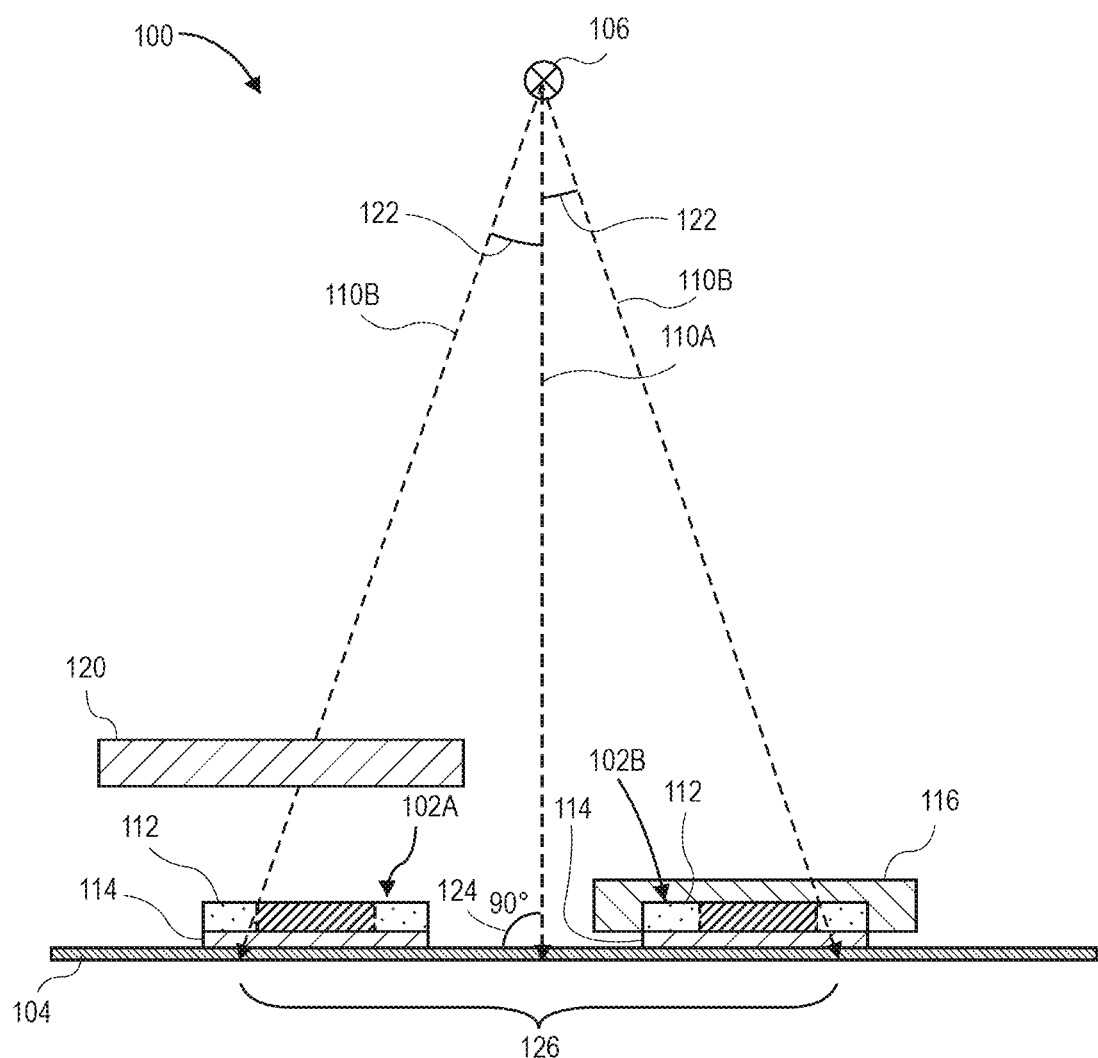
FIG. 1 illustrates a schematic view of an image quality indicator (IQI) system, according to an embodiment.

Reference will now be made in detail to specific embodiments illustrated in the accompanying drawings and figures. In the following detailed description, numerous specific details are set forth in order to provide a thorough understanding of the embodiments described herein. However, it will be apparent to one of ordinary skill in the art that other embodiments may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object could be termed a second object, and, similarly, a second object could be termed a first object, without departing from the scope of the present disclosure.

The terminology used herein is for the purpose of describing particular embodiments only and is not intended to be limiting. As used in the description and the appended claims, the singular forms "a," "an" and "the" are intended to include the plural forms as well, unless the context clearly indicates otherwise. It will also be understood that the term "and/or" as used herein refers to and encompasses any and possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, operations, elements, components, and/or groups thereof. Further, as used herein, the term "if" may be construed to mean "when" or "upon" or "in response to determining" or "in response to detecting," depending on the context.

As used herein, the terms "inner" and "outer"; "up" and "down"; "upper" and "lower"; "upward" and "downward"; "above" and "below"; "inward" and "outward"; and other like terms as used herein refer to relative positions to one another and are not intended to denote a particular direction or spatial orientation. The terms "couple," "coupled," "connect," "connection," "connected," "in connection with," and "connecting" refer to "in direct connection with" or "in connection with via one or more intermediate elements or members."

The systems and methods disclosed herein are directed to an image quality indicator (IQI) system that is configured to detect cracks in a part using radiography testing, such as x-ray radiography. The IQI system may include a relatively inexpensive crack image quality indicator (crack IQI) that includes a component part with simulated cracks of different sizes. The component part may be a metallic part or a non-metallic part. The metallic part be made of titanium, aluminum, stainless steel, carbon steel, Inconel, and other metal alloys.

The IQI system may perform radiography testing on the crack IQI. This may be referred to as a qualification test. Based upon the simulated cracks in the crack IQI that the IQI system is able to detect, the minimum crack size detectable by the IQI system may be determined. After qualifying that the IQI system can detect cracks of at least the minimum size, the IQI system may then be used to perform radiography testing on an actual component to detect cracks in the actual component that are greater than or equal to the minimum crack size. This may be referred to as an inspection test.

The crack IQI may include a hole-plug penetrameter (HPP), which may simulate the crack. The HPP may include first body (e.g., a washer) and a second body (e.g., a plug) that is configured to be inserted in the washer to form a hole-plug interface having an interface gap. The interface gap of the HPP has a predetermined interface gap width that simulates a predetermined crack size in the component part to be inspected.

FIG. 1 illustrates a schematic view of an IQI system 100 including one or more crack IQIs (two are shown: 102A, 102B), a film 104, and a radiation source 106. The crack IQIs 102A, 102B may be positioned within the IQI system 100. More particularly, the crack IQIs 102A, 102B may be positioned at least partially between the film 104 and the radiation source 106. When the crack IQIs 102A, 102B are in the IQI system 100, the IQI system 100 may be in an IQI physical set-up. When in the IQI physical set-up, the IQI system 100 may be configured to perform a qualification test to detect one or more simulated cracks in the crack IQIs 102A, 102B. Based upon the one or more simulated cracks detected during the qualification test, the minimum crack size detectable by the IQI system 100 may be determined. The IQI system 100 may then be used in an inspection physical set-up where the crack IQIs 102A, 102B are replaced by actual component parts. When in the inspection physical set-up, the IQI system 100 may perform an inspection test on the actual component part to detect one or more cracks therein that are greater than or equal to the minimum crack size.

The radiation source 106 is configured when in the IQI physical set-up to generate radiation rays 110A, 110B directed to the crack IQIs 102A, 102B and/or the film 104. The film 104 may be a radiation detector (also referred to as an imaging detector) that is configured to detect radiation transmitted from the radiation source 106, and to record a detected IQI radiographic image. The radiation detector may be embodied by a film, computed radiography (CR) imaging plate, digital detector (DR) panels, and/or other digital and non-digital devices. The crack IQIs 102A, 102B may be used to simulate a (real) component part having predetermined crack characteristics, such as a predetermined crack size. The radiation source 106 transmits radiation rays 110A, 110B that pass through the crack IQIs 102A, 102B and to the film 104, which records a detected image. The detected image may correspond to crack characteristics of the crack IQIs 102A, 102B.

FIG. 1 shows two crack IQIs 102A, 102B spaced apart from one another. Each crack IQI 102A, 102B includes a hole-plug penetrameter (HPP) 112 and, in some embodiments, a shim 114. The shim 114 may be positioned adjacent to the HPP 112 so that the combination of the HPP 112 and the shim 114 are configured to have the thickness of the actual component part to be tested during the inspection test. In the crack IQI 102B, a resin mounting 116 may at least partially cover the HPP 112.

In the IQI physical set-up, the crack IQIs 102A, 102B are positioned adjacent the film 104, and the radiation source 106 is positioned to direct at least a portion of the rays 110A, 110B to the HPP 112. The rays include one or more normal rays 110A and one or more limit rays 110B. The normal ray 110A forms a right angle 124 with an outer surface of the film 104. The limit rays 110B form limit angles 122 with the normal ray 110A. The limit rays 110B may determine the extent of an inspection coverage length 126 that forms a verified inspection area. The IQI system 100 may perform an inspection to detect the simulated crack of the image quality indicator 102 positioned in the verified inspection area, as shown in FIG. 1.

More than one crack IQI 102A, 102B may be used to simulate cracks for the IQI system 100 in a IQI physical set-up. In addition, the IQI physical set-up may simulate different component parts. For example, the IQI physical set-up may simulate a single wall component, a double wall component, or other multiple wall component having more than two walls. In FIG. 1, a wall shim 120 is spaced from the crack IQI 102A with the wall shim 120 disposed between the radiation source 106 and the film 104. The wall shim 120 and the crack IQI 102A simulate a component part that has a double wall.

The IQI physical set-up and the inspection physical set-up may have substantially similar (e.g., identical) set-up parameters. The set-up parameters may include the distance between the radiation source 106 and the crack IQIs 102A, 102B in the IQI physical set-up, and the distance between the radiation source 106 and the actual component part in the inspection physical set-up. The set-up parameters may also include the angles of the normal rays 110A and/or the limit rays 110B in the IQI physical set-up and the inspection physical set-up. The set-up parameters may also include the energy level of the IQI physical set-up and the inspection physical set-up (e.g., from about 40 keV to about 10 MeV). The set-up parameters may also include the exposure of the IQI physical set-up and the inspection physical set-up (e.g., milliampere×time). The current may be from about 1 mA to about 20 mA, and the time may be from about 1 second to about 60 minutes. The set-up parameters may also include the distance between the source 106 and the film 104 of the IQI physical set-up and the inspection physical set-up. The distance may be from about 1 foot to about 10 feet. The set-up parameters may also include the source 106 of the IQI physical set-up and the inspection physical set-up. The source 106 may be or include nano-focus sources, micro-focus sources, milli-focus sources, tube sources, radioactive material sources, or a combination thereof. The set-up parameters may also include the screen of the IQI physical set-up and the inspection physical set-up. The screen may be or include a lead screen. The set-up parameters may also include the collimation of the IQI physical set-up and the inspection physical set-up. The collimation may be or include a lead tube or cone to prevent scattered radiation from reaching the detector. The set-up parameters may also include the masking of the IQI physical set-up and the inspection physical set-up. The masking may be or include a heavy density material that absorbs unwanted radiation such as lead shot. The set-up parameters may also include the filters of the IQI physical set-up and the inspection physical set-up. The filters may be or include various materials such as copper, aluminum sheets of varying thickness placed next to the source x-ray exit point. The filters may absorb low energy radiation. The set-up parameters may also include the film/detector type/specification of the IQI physical set-up and the inspection physical set-up. The detector may be or include x-ray imaging film, a CR imaging plate, a DR imaging detector, or a combination thereof. The set-up parameters may also include the film processing parameters of the IQI physical set-up and the inspection physical set-up. The film processing parameters may be or include temperature and time.

Figure 2:
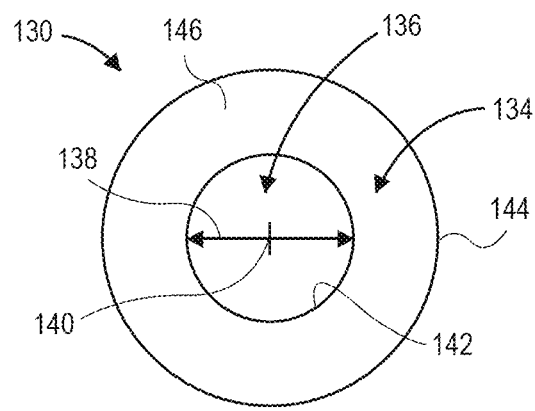
FIG. 2 illustrates a top view of a washer of a hole-plug penetrameter (HPP) of the IQI system in an unassembled position, according to an embodiment.
Figure 3:
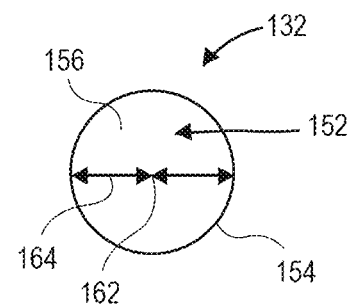
FIG. 3 illustrates a top view of a plug of the HPP of the IQI system in the unassembled position, according to an embodiment.

Referring to FIG. 2 and FIG. 3, a top view of components of the HPP 112 in a disassembled configuration is shown. The HPP 112 may include a first (e.g., outer) body 130, shown in FIG. 2, and a second (e.g., inner) body 132, shown in FIG. 3. The first body 130 may be referred to herein as a washer, and the second body 132 may be referred to herein as a plug. The washer 130 has a washer body 134 that forms a washer hole 136 that extends through the washer body 134. A center axis 140 of the washer body 134 extends through the washer hole 136. The washer 130 further has an inner surface 142 surrounding the washer hole 136, a washer outer surface 144, a washer top surface 146, and a washer bottom surface 148 (shown in FIG. 5). The inner surface 142 has an inner surface diameter 138. As shown in FIG. 2, the washer 130 may have a cylindrical shape with the washer body 134 forming the washer hole 136 in a cylindrical shape. In other embodiments, the washer 130 may have other shapes, including rectangular shapes.

Figure 4:
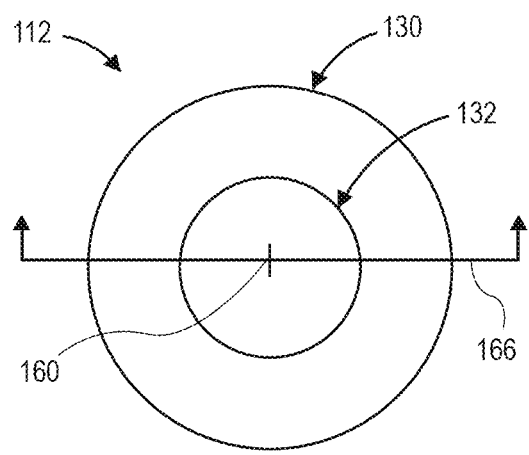
FIG. 4 illustrates a top view of the HPP in an assembled position, according to an embodiment.

As shown in FIG. 3, the plug 132 has a plug body 152 in a cylindrical shape. In some embodiments, the plug 132 may have other shapes, including rectangular shapes. The plug body 152 has a plug outer surface 154, a plug top surface 156, and a plug bottom surface 158 (shown in FIG. 5). The plug body 152 has a plug center axis 162 that extends through plug body 152 from the plug top surface 156 to the plug bottom surface 158 (shown in FIG. 5), and a plug outer diameter 164. The plug 132 is sized to be fit in the washer 130 in an assembled position, as shown in FIG. 4. The plug 132 may be sized with the plug outer diameter 164, also referred to as $D_{plug}$, that is less than the inner surface diameter 138, also referred to a $D_{hole}$ of the washer 130 (e.g., forming a frictionless assembly). The temperature of the washer 130, plug 132, or both may then be varied (e.g., a temperature differential therebetween may decrease and/or equalize) to create an interference assembly.

Figure 5:
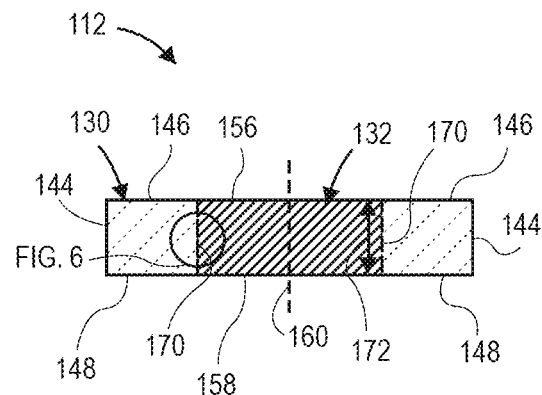
FIG. 5 illustrates a cross-sectional view of the HPP of FIG. 4, according to an embodiment.

Referring to FIG. 4 and FIG. 5, the HPP 112 is shown in an assembled configuration. The plug 132 is inserted in the washer hole 136 in the assembled configuration. In some embodiments, the HPP 112 is made by assembling the plug 132 in the washer hole 136 of a washer 130 of the same thickness in a shrink or force fit fashion. FIG. 4 shows a top view of the HPP 112. A cross-section line 166 extends through an HPP center axis 160. The HPP center axis 160 may extend through and align with the center axis 140 of the washer 130 and the center axis 162 of the plug 132.

FIG. 5 shows a cross section of the HPP 112 along the cross-section line 166 in FIG. 4. The HPP 112 has a hole-plug interface 170 where the plug outer surface 154 is adjacent to (e.g., contacts) the washer inner surface 142. The hole-plug interface 170 may have a predetermined interface length. In FIG. 5, the hole-plug interface 170 extends through the HPP 112 and has an interface length 172 extending from top surfaces 146, 156 to bottom surfaces 148, 158. The interface length (also referred to as the interface depth) 172 may extend through only a portion of the HPP 112 in some embodiments. The hole-plug interface 170 in FIG. 5 is at a normal angle to the top surface 156 and the bottom surface 158 that it intersects. The hole plug interface 170 may simulate a crack having predetermined characteristics, such as a crack width and crack length.

Figure 6:
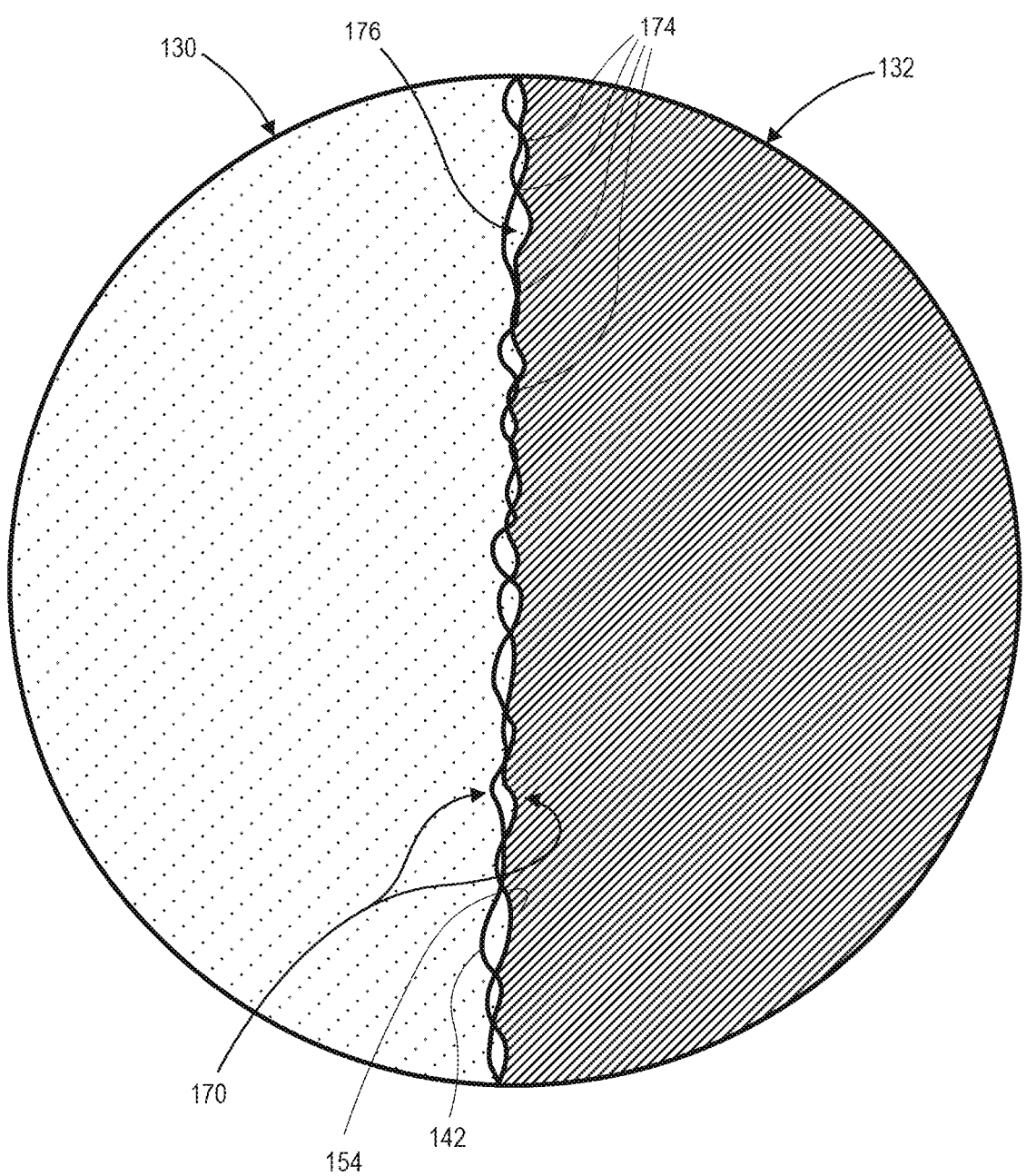
FIG. 6 illustrates an enlarged view of a section of the HPP of FIG. 5 showing a hole-plug interface, according to an embodiment.

Referring to FIG. 6, an enlarged view of a section of the hole-plug interface 170, according to an embodiment, is shown. The washer inner surface 142 is adjacent to (e.g., contacting) the plug outer surface 154 at the hole-plug interface 170. One or more interface gaps 176 may be formed between the washer inner surface 142 and the plug outer surface 154. The interface gaps 176 may be formed along the length of hole-plug interface 170.

The plug 130 and the washer 132 may have a friction/interference fit to form the interface gaps 176 where the washer internal surface 142 contacts the plug outer surface 154 at one or more intermittent contact points 174, as shown in FIG. 6. The interface gaps 176 may be formed between the intermittent contact points 174. The sections of the hole-plug interface 170 where there is no contact between the washer inner surface 142 and the plug outer surface 154 form the gaps 176. The width of the interface gaps 176 may be determined by the size and number of the intermittent gaps 176 along the length of hole-plug interface 170. The size and number of intermittent gaps 176 may be due to surface finish of the washer inner surface 142 and the plug outer surface 154 that mate with one another. A rougher surface finish increases the width of the interface gaps 176, and a smoother surface finish decreases the width of the interface gaps 176. In some embodiments, the interface gaps 176 of the image quality indicator 102A may not have contact points between the washer inner surface 142 and the plug outer surface 154.

The interference fit between the outer diameter of the plug 132 ($D_{plug}$) and the inner diameter of the washer hole 136 ($D_{hole}$) may be referred to as the radial interference $\delta_0$. The radial interference is given by:

$$(\delta_0=(D_{plug}-D_{hole})/2 \qquad \text{(equation 1)}$$

The other parameters for the interference fit may include surface finish, straightness, and roundness. The hole-plug interface 170 between the plug 132 and the washer hole 136 provides a cracklike discontinuity in terms of crack gap width W and depth a. The shim 114 provides the a/t ratio that is to be detected, where t is the thickness of the component part.

The crack IQIs 102A, 102B may have a predetermined interface gap width. The interface gap width of the crack IQIs 102A, 102B is selected to simulate a gap width of a crack in a component part. The plug-hole interface 170 may simulate a crack that is normal to the top surfaces 146, 156 and/or the bottom surfaces 148, 158 of the HPP 112.

The IQI system 100 may include a plurality of HPPs (also referred to as an HPP set) 112. The HPP set may include multiple HPPs 112 that simulate different cracks. For example, each HPP 112 may simulate a crack having a different crack width. The crack width also may be referred to as an interface gap width. The interface gap width of one of the HPPs 112 may be determined by using a microscope or scanning electron microscope (SEM) to measure the interface gaps 176 along different points of the length of the hole-plug interface 170. An HPP 112 may be sectioned normal to the length of the interface gap 176 to measure the width of the interface gap 176 at a selected point along the length of the interface gap 176. A protocol for measuring the width of the interface gap 176 may be used to determine the interface gap width of the HPPs 112. Statistical quantities such as mean and standard deviation of measurements along the length of the interface gap 176 may be used in determining the interface gap width for the HPPs 112.

The HPPs 112 may be classified based on interface gap widths. In some embodiments, an interface gap classification based on interface gap widths is used. The interface gap classification includes different interface gap classes with each class including a minimum interface gap width and a maximum interface gap width. The range of interface gap widths for the HPPs 112 are different for each interface gap class. An example HPP classification with different interface gap classes is shown in Table 1—HPP Classification:

TABLE 1

| HPP Classification | | |
| --- | --- | --- |
| Interface Gap Class | Min. Interface Gap, mil | Max. Interface Gap, mil |
| 1 | 0.025 | 0.05 |
| 2 | 0.05 | 0.10 |
| 3 | 0.1 | 0.2 |
| 4 | 0.2 | 0.4 |
| 5 | 0.4 | 0.8 |
| Custom | TBD | TBD |

The maximum and minimum interface gap size for a class (where cl=class) is given by:

$$W_{max}=0.05\times 2^{cl-1} \qquad \text{(equation 2)}$$

$$W_{min}=0.025\times 2^{cl-1} \qquad \text{(equation 3)}$$

A custom class is also added so that the interface gap specification can be tailored. The ranges may be exclusive in these classes, and the mean±3 times standard deviation are expected to be within these ranges for the crack IQI. Lower numbers are considered to be finer classes, and higher number are considered to be courser classes.

Figure 7:
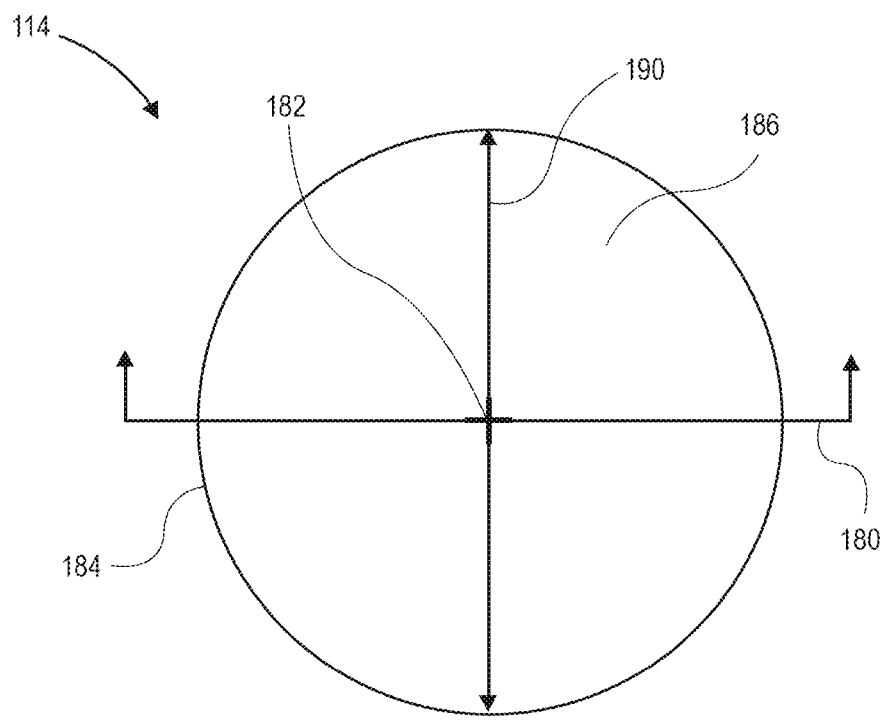
FIG. 7 illustrates a top view of a shim of the IQI system, according to an embodiment.
Figure 8:
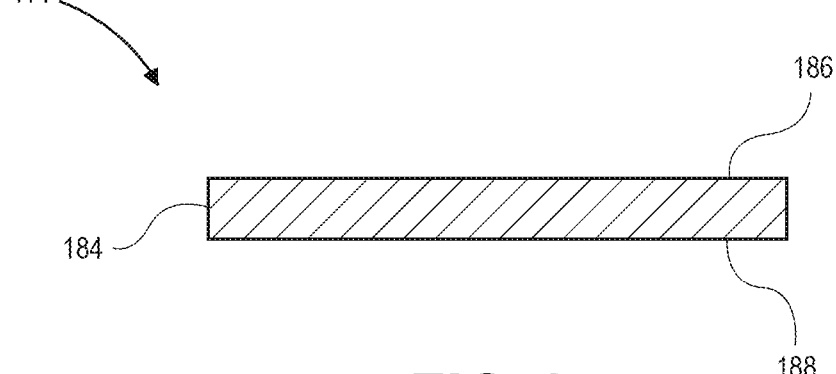
FIG. 8 illustrates a cross-sectional view of the shim of FIG. 7, according to an embodiment.

Referring to FIG. 7 and FIG. 8, the shim 114 is shown. FIG. 7 shows a top view of the shim 114, and FIG. 8 show a cross-sectional view of the shim 114 at the cross-sectional line 180 in FIG. 7. The shim 114 may have a cylindrical shape, as shown in FIG. 7. In some embodiments, the shim 114 may have other shapes, including rectangular shapes. The shim 114 has a shim outer surface 184, a shim top surface 186, and a shim bottom surface 188 (shown in FIG. 8). The shim 114 has a shim center axis 182 that extends through shim 114 from the shim top surface 186 to the shim bottom surface 188 (shown in FIG. 8), and a shim outer diameter 190.

Figure 9:
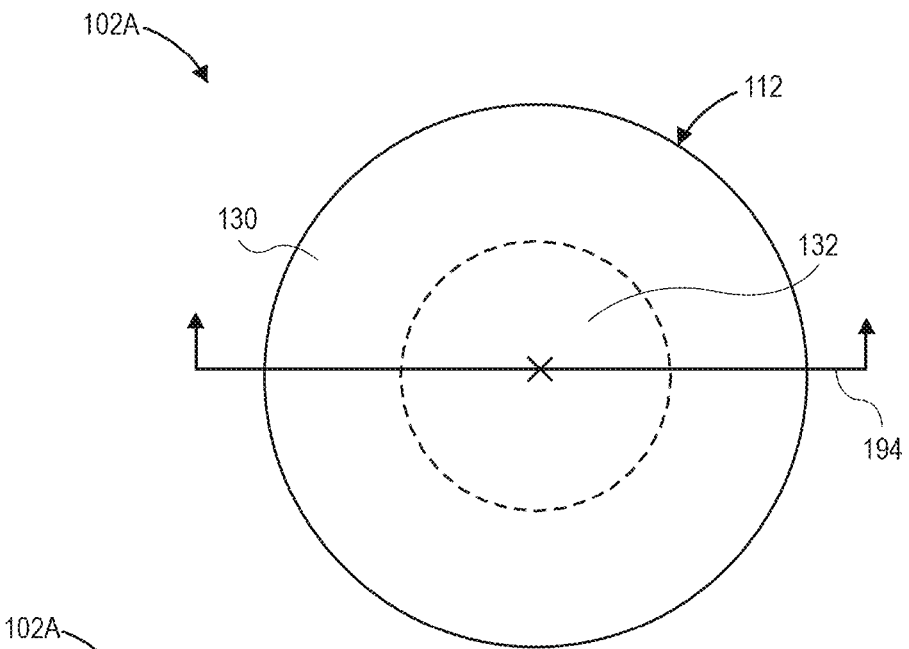
FIG. 9 illustrates a top view of the IQI system in the assembled position, according to an embodiment.
Figure 10:
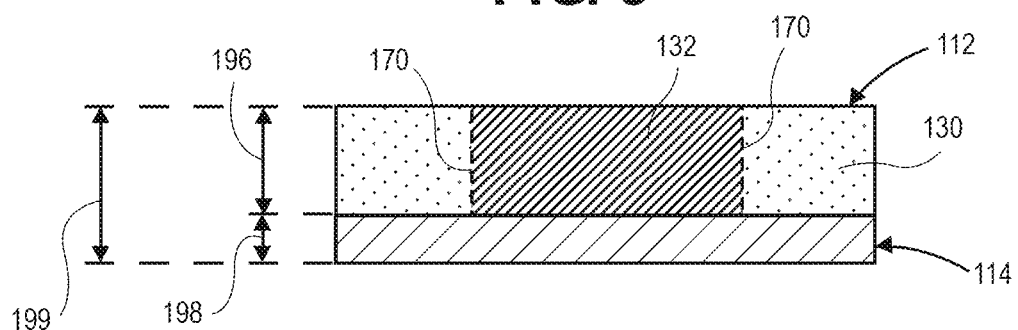
FIG. 10 illustrates a cross-sectional view of the IQI system of FIG. 9 showing the HPP and the shim stacked together, according to an embodiment.

Referring to FIG. 9 and FIG. 10, the crack IQI 102A (or 102B) having the HPP 112 stacked on the shim 114 is shown. FIG. 9 is a top view of the crack IQI 102A, and FIG. 10 is a cross-sectional view at cross-sectional line 194 in FIG. 9. The HPP 112 has an HPP thickness 196, and the shim 114 has a shim thickness 198. The crack IQI 102A has an IQI thickness 199 that is the sum of the HPP thickness 196 and the shim thickness 198. The IQI thickness 199 of the crack IQI 102A may simulate a component part that is to be tested after performing a qualification test using the crack IQI 102A simulating the component part.

In operation, the IQI system 100 may be used in a qualification test to determine that the IQI system 100 positioned in a crack IQI physical set-up can detect simulated cracks of a predetermined characteristic of the crack IQIs 102A, 102B, such as crack width. The crack IQIs 102A, 102B provide simulated cracks in a material and geometry that is like the actual component part to be tested, and provide the IQI physical set-up that is also like the part physical set-up. In other words, the IQI physical set-up is configured to be similar to the part physical set-up. The qualification test (also referred to as an IQI test) may be performed using IQI physical set-up with the crack IQIs 102A, 102B simulating a component part in the part physical set-up. The IQI test is used to verify the detectability of cracks having a minimum characteristic in a component part in the part physical set-up. For example, the test procedure may be verified to detect cracks having a predetermined minimum size (e.g., width and/or length). A component part test is performed using the part physical set-up that has been verified by the IQI test to detect cracks of a minimum predetermined size.

Figure 11:
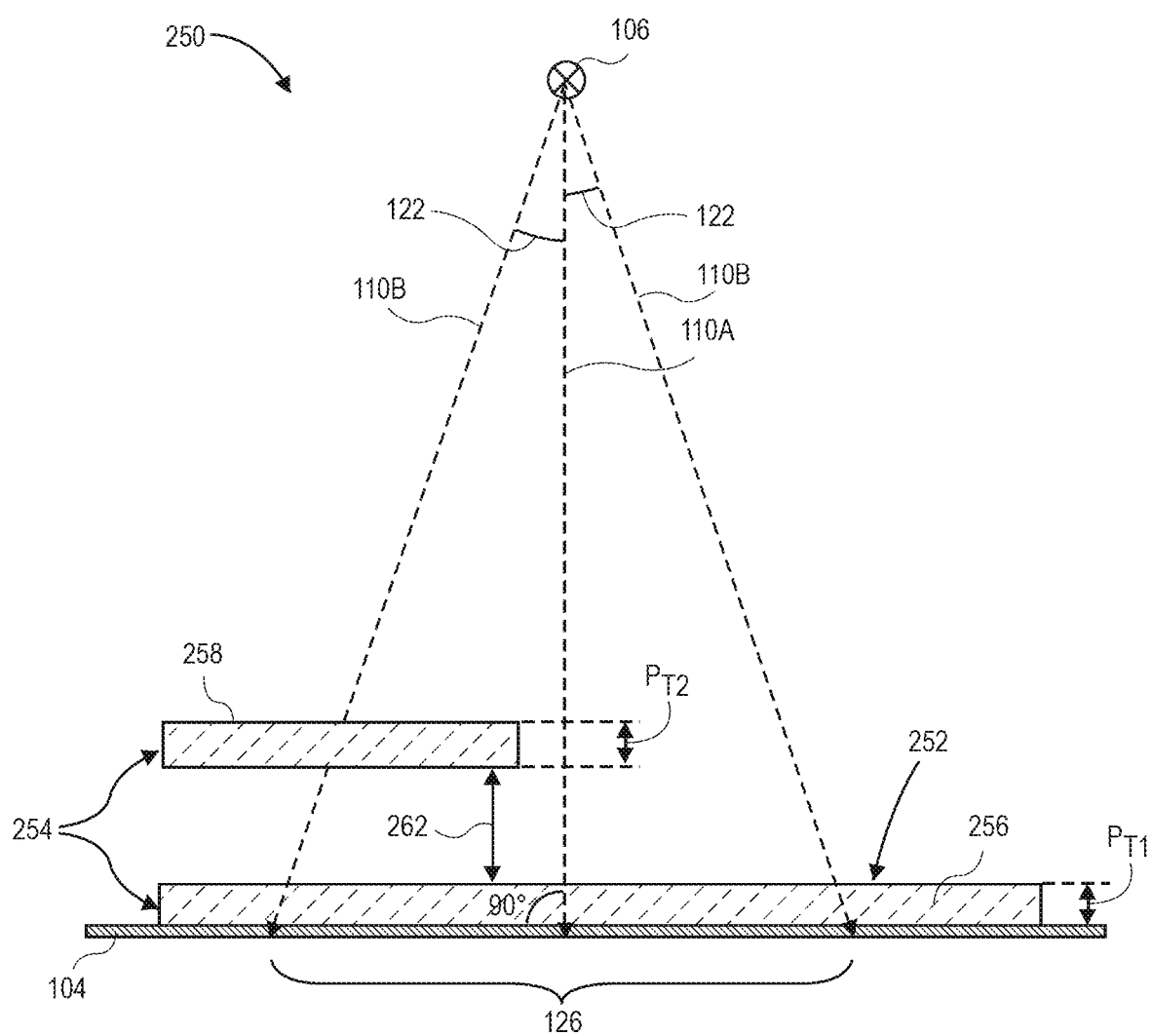
FIG. 11 illustrates a schematic view of a part inspection system in a part physical set-up, according to an embodiment.
Figure 12:
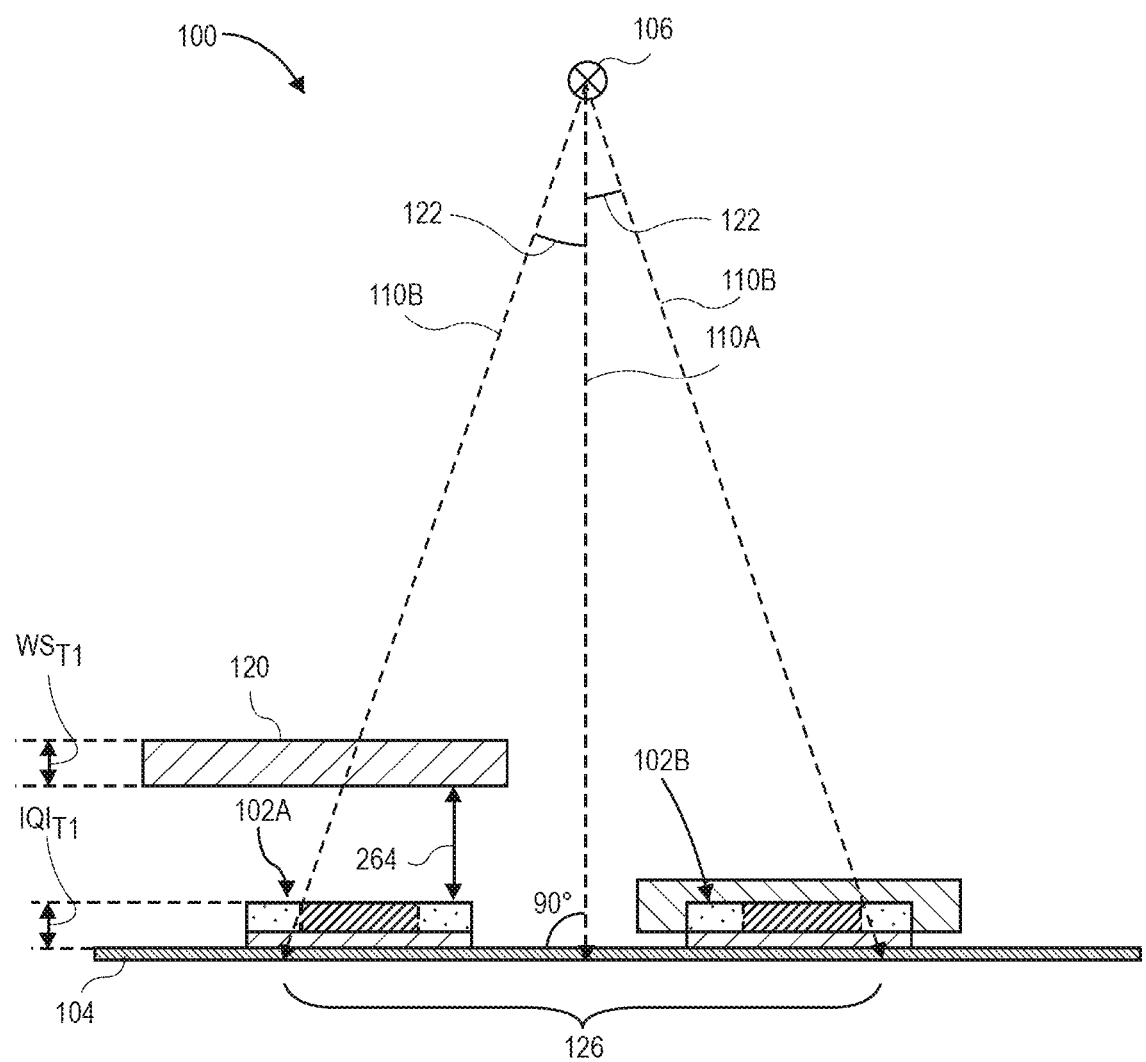
FIG. 12 illustrates a schematic view of the IQI system in an IQI physical set-up, according to an embodiment.

Referring to FIG. 11 and FIG. 12, a part inspection system 250 in a part physical set-up is shown in FIG. 11. The part inspection system 250 includes at least one component part to be inspected for cracks. In FIG. 12, the IQI system 100, previously described with respect to FIG. 1 in an IQI physical set-up is shown. The IQI system 100 in the IQI physical set-up simulates the part physical set-up of the part inspection system 250. The part inspection system 250 and the IQI system 100 have similar physical set-ups. The physical set-ups are configured to be alike so that qualification tests performed using the IQI system 100 may verify that cracks sized at least at the minimum crack size qualified by the IQI system 100 will be detected during an inspection of the component part in the part inspection system 250 having the part physical set-up.

In the part inspection system 250 of FIG. 11, the component part to be tested for cracks includes a single-wall part 252 and a double-wall part 254. The single-wall part 252 and double-wall part 254 may share a first wall 256, and the double-wall part 254 further includes a second wall 258. The first wall 256 has a first wall thickness of $P_{T1}$. The second wall 258 has a second wall thickness of $P_{T2}$. The component part is positioned adjacent and may abut a radiation detector, such as the film 104.

The radiation source 106 may be spaced a predetermined distance and location from the double wall part 254 and/or the single wall part 252 forming the component part. The portion of the component part being tested is positioned within the area covered by radiation rays 110A, 110B in an IQI coverage area. The IQI coverage area is defined by the limit radiation rays 110B, also referred to as the IQI verified coverage length.

In some embodiments, the radiation source 106 used in the inspection physical set-up for the part inspection system 250, shown in FIG. 11, is the same radiation source 106 used in the IQI physical set-up for the IQI system 100, shown in FIG. 12. In other embodiments, two (e.g., different) radiation sources 106 may be used: a first radiation source 106 for the part inspection system 250, and a second radiation source 106 for the IQI system 100. The first radiation source 106 and the second radiation source 106 may be identical or like one another. The radiation source 106 of the part inspection system 250 is configured to generate radiation rays 110A, 110B directed to the wall parts 252, 254 and/or the film 104. The film 104 is a radiation detector and is configured to detect radiation transmitted from the radiation source 106 and to record a detected part radiographic image. The radiation source 106 transmits radiation rays 110A, 110B that pass through the wall parts 252, 254 of the component part and to the film 104 that records a detected image. The indication of cracks in the component part may be recorded on the detected image.

To verify that the component part test will detect cracks of a minimum predetermined characteristic, an IQI test is performed using the IQI physical set-up. In the IQI physical set-up of FIG. 12, a first IQI and a second IQI simulate the component parts, shown in FIG. 11, to be tested for cracks in the crack inspection test. The first IQI and the second IQI are positioned adjacent the film 104 and may have the same thickness as the single wall part 252 shown in FIG. 11. The wall shim, referred to as the second wall shim in FIG. 12, may be spaced from the first IQI. The wall shim may be spaced from the first IQI a distance to simulate the part double wall shown in FIG. 11. The IQI physical set-up is further described with respect to FIG. 1.

The part physical set-up, shown in FIG. 11, and the IQI physical set-up, may be identical for single wall and double (or multiple) wall x-ray inspection. The x-ray shot technique (mA, KV, shot duration) may also be same. In a double wall exposure with single wall reading shots, an additional shim representing the part wall on the radiation source side may be used. For a component part having a double wall, a first IQI may be used to simulate a first wall of the double wall, and a second IQI may be used to simulate a second wall of the double wall. The farthest simulated crack (e.g., hole-plug interface 170) of the crack IQI is located at the limit x-ray ray angle. This arrangement determines the extent of inspection coverage length as verified by detection of the simulated crack of the crack IQI.

The part physical set-up may be verified for a minimum predetermined crack characteristic, such as a minimum crack length, a minimum crack depth, and/or a minimum crack gap/width. The crack IQI may be selected based on the minimum predetermined crack characteristic. For example, a selected crack gap width may be used to select a crack IQI falling in the interface gap class covering the selected crack gap width. For example, if the selected crack gap width falls in the first interface gap class, then a crack IQI classified as a first interface gap class may be selected for the IQI physical set-up.

The IQI test is performed by transmitting radiation rays 110A, 110B from the radiation source 106 to the crack IQI or multiple crack IQIs 102A, 102B in the verified coverage area of the IQI physical set-up. The radiation rays 110A, 110B may be detected by the radiation detection, such as the film 104, and a crack image is saved by the radiation detector. The crack image may be indicative of crack characteristics of the simulated crack, such as crack gap width. A crack image recorded by the radiation detector may indicate that the IQI physical set-up is detecting a minimum crack characteristic, such as crack gap width. The IQI test detecting the selected minimum crack characteristic may be used to verify that the IQI set-up, and the part physical set-up may detect cracks having the selected or predetermined minimum crack characteristic. The qualification test provides a verification of the detectability of cracks of a minimum characteristic when performing a component part test on a physical component tested in the part physical set-up simulated by the IQI physical set-up. A component part test that has been verified by the IQI test may be performed on a component part.

Figure 13:
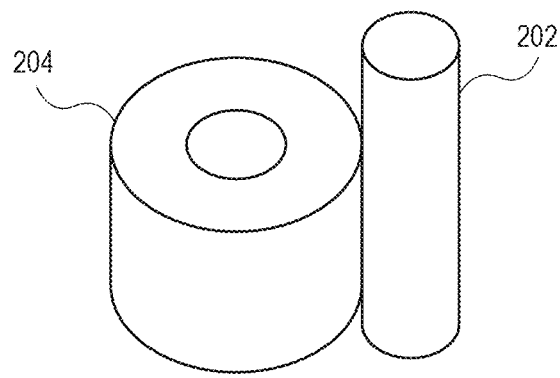
FIG. 13 illustrates a perspective view of a pipe-shaft assembly, including a pipe and a shaft, in an unassembled position, according to an embodiment.
Figure 14:
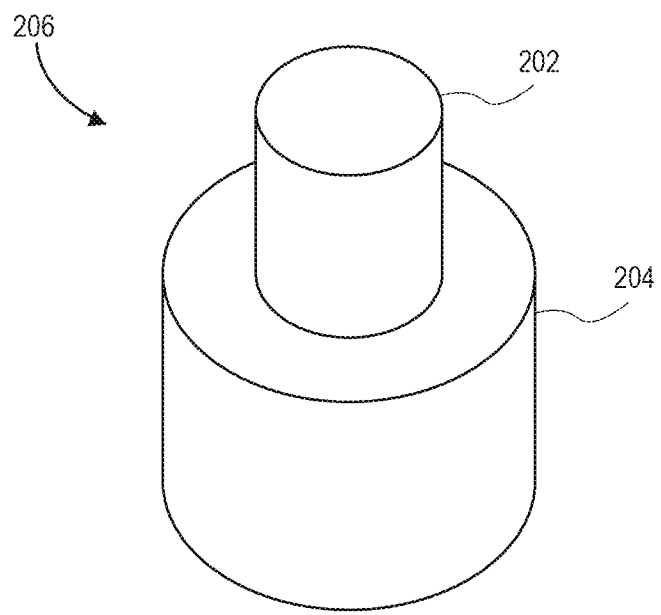
FIG. 14 illustrates a perspective view of the pipe-shaft assembly in an assembled position, according to an embodiment.

The HPP 112 of the crack IQIs 102A, 102B may be manufactured to provide a plurality of HPPs 112 forming an HPP set with each HPP 112 having the same crack gap width and either the same HPP thickness or different HPP thicknesses. Referring to FIG. 13 and FIG. 14, an HPP set, including one or more HPPs 112, may be assembled with a shaft 202 and a pipe 204. FIG. 13 is perspective view of the shaft 202 and the pipe 204 in an unassembled position. FIG. 14 is a perspective view showing the shaft 202 inserted in the pipe 204 in a pipe-shaft assembly 206.

Referring to FIG. 15 and FIG. 16, the pipe 204 may be elongated and have a cylindrical shape. In some embodiments the pipe 204 may have other geometries, including a rectangular or oval shape. FIG. 15 is a front side view of the pipe 204, and FIG. 16 is an end view of the pipe 204 in a disassembled configuration. The pipe 204 has a pipe body 208 having a pipe opening 210 that extends through the pipe body 208. A center axis 212 of the pipe body 208 extends through the pipe opening 210. The pipe 204 further has an inner surface 214 surrounding the pipe opening 210, a pipe outer surface 216, a first end surface 220, and an opposite second end surface 222. The inner surface 214 has an inner surface diameter 224. The outer surface 216 has an outer surface diameter 226.

As shown in FIG. 17 and FIG. 18, the shaft 202 has a shaft body 230 in a cylindrical shape. In some embodiments, the shaft 202 may have other shapes, including rectangular shapes. The shaft body 230 has a shaft outer surface 232, a shaft first end surface 234, and a shaft second end surface 236. The shaft body 230 has a shaft center axis 240 that extends through the shaft body 230 from the first end surface 234 to the second end surface 236, and a shaft outer diameter 242.

The shaft 202 is sized to be fit in the pipe 204 in a pipe-shaft assembly 206, as shown in FIG. 19 and FIG. 20, to form a hole-plug interface 170 where the shaft outer surface 232 and the pipe inner surface 214 are adjacent one another. A pipe outer radius $r_1$ and a pipe inner radius $r_2$ is shown. A predetermined interface gap 176, depicted in FIG. 6, is formed at the hole-plug interface 170. The interface gap 176 may have a predetermined interface gap width that is in a selected interface gap class, such as shown in above Table 1. A plurality of pipe-shaft assemblies 206 may be manufactured with each of the manufactured pipe-shaft assemblies 206 having a predetermined interface gap 176 in a different one of the interface gap classes.

The pipe-shaft assembly 206, shown in FIG. 19, may be cut normal to the center axis 212 at spaced intervals along the length of the pipe-shaft assembly 206 to create multiple HPPs 112, shown in FIG. 21. Each of the HPPs 112 may by in a selected interface gap class. Each of the HPPs 112 may have the same predetermined interface gap width that falls in the selected interface gap class. Each of the HPPs 112 may be manufactured to simulate a crack in a component part having a predetermined crack gap width.

The pipe-shaft assembly 206 may be cut at spaced intervals along the pipe-shaft assembly 206 to form individual HPPs 112 having different HPP depths or thicknesses. In FIG. 21, eight HPPs 112 are shown with an HPP 112A having an HPP thickness T1, and an HPP 112B having an HPP thickness T2. The HPP thickness T1 is greater than the HPP thickness T2. In some embodiments, the HPPs 112 have the same thickness. The HPPs 112 manufactured from the pipe-shaft assembly 206, shown in FIG. 19, form an HPP set 246 of a plurality of HPPs 112 of the same interface gap class with the same or different thicknesses. An HPP set 246 with HPPs 112 of different thicknesses may allow for more versatility in simulating component parts of different thicknesses.

Since multiple HPPs 112 may be made from the single pipe-shaft assembly 206, one or more of the HPPs 112 may be used to measure the interface gap 176. In some embodiments, the measurement may be made by destructive testing. If the interface gap measurements are consistent in the cut-up samples, then depending on the interface gap measurements, a class may be assigned to the remaining HPPs 112 made from the corresponding pipe-shaft assembly 206. Thus, the HPP classification may be based on destructive measurement interface gaps of samples from each pipe-shaft assembly 206.

Referring again to FIG. 1, in some embodiments, a resin mounting 116 may be applied to the washer 130 and/or the plug 132. The resin mounting 116 may be applied to encase the washer 130 and/or the plug 132 to secure the plug 132 in the washer 130. The resin mounting 116 may be made of an acrylic material or other non-metallic material. The resin mounting 116 may be left as-is after manufacturing, and may be made of materials that allow the resin mounting 116 to remain in place when the HPP 112 is used in a qualification test. The effect of the resin mounting 116 on x-ray imaging during a qualification test using the HPP 112 may be tolerable due to its lower density material compared to the material of the washer 130 and plug 132.

Figure 22:
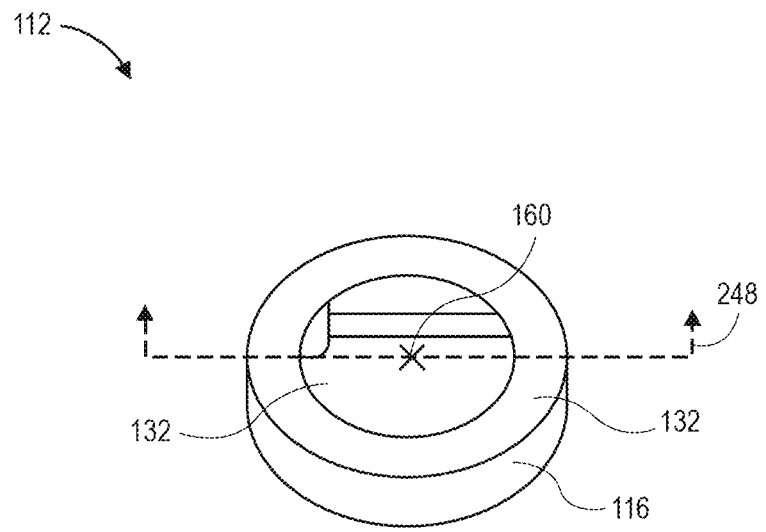
FIG. 22 illustrates a perspective view of the IQI having a resin mold, according to an embodiment.
Figure 23:
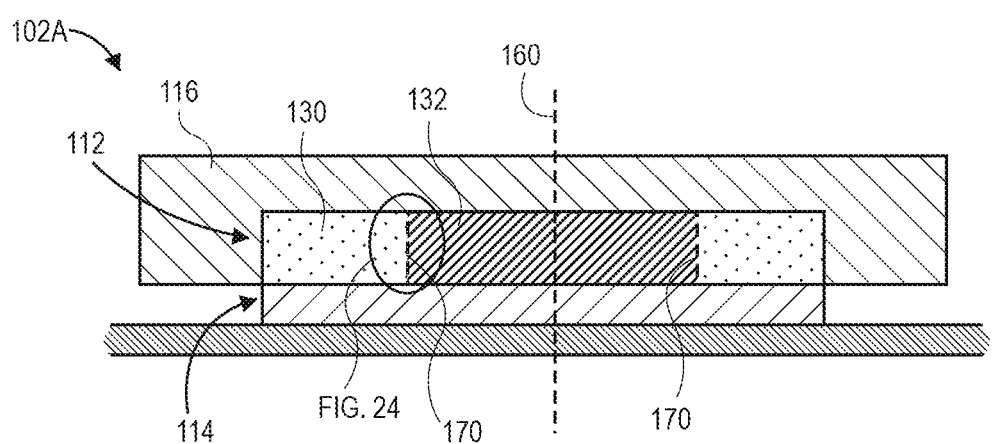
FIG. 23 illustrates a cross-sectional view of the IQI of FIG. 22, according to an embodiment.

Referring to FIG. 22 and FIG. 23, an HPP 112 with the resin mounting 116 is shown. FIG. 22 shows a perspective view of the HPP 112. FIG. 23 shows a cross-sectional view of the crack IQI 102A with the HPP 112 stacked on the shim 114 and placed adjacent the film 104. The cross-sectional view of the HPP 112 shown in FIG. 23 is taken at the cross-sectional line 248 of FIG. 22. The cross-sectional line 248 extends through the HPP center line 160 of FIG. 22.

Figure 24:
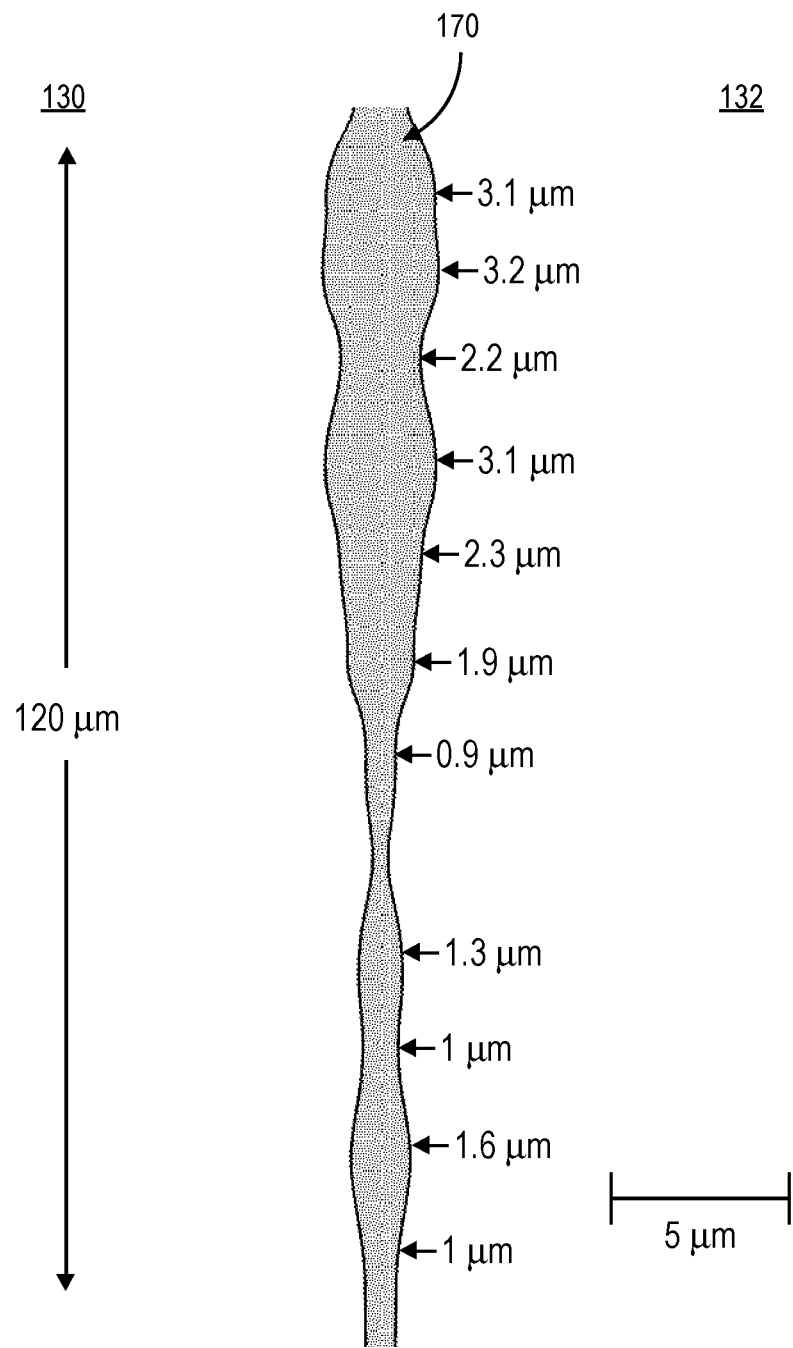
FIG. 24 illustrates an enlarge view of a hole-plug interface shown in FIG. 23, according to an embodiment.

Referring to FIG. 24, an enlarged section of an HPP hole-plug interface 170 cross-section is shown. Measurements of the interface gap width at discrete locations along the hole-plug interface 170 may be made with a microscope. These interface gap widths are shown at the discrete locations along the hole-plug interface 170 in FIG. 24. For example, an interface gap width is identified as 3.1 µm at a top discrete location, and an interface gap width of 1 µm is shown at a bottom discrete location. The discrete interface gap widths, shown in FIG. 24, are part of the interface gap distribution for the HPP 112 that has been cut along cross-sectional line 248 in FIG. 22. This destructive testing of the HPP 112 may be used to determine the interface gap width for the remaining HPPs 112 in an HPP set 246. The interface gap width for the hole-plug interface 170 of the HPP 112 may be based on the discrete interface gap widths measured. The determination of the hole-plug interface width of the HPP 112 may include using the interface gap distribution mean and/or standard deviation calculations of the discrete interface gap widths.

The hole-plug interface 170 may be sectioned normal to the length of the hole-plug interface 170 and through the center of the crack to measure the crack gap in depth direction. The gap measurement surface may be prepared to be flat and smooth by lapping or grinding. If the surface is smeared, then a light chemical etching may be performed to remove the smear. This process may be performed in a metallography laboratory. Thus, if an x-ray technique is to be used to detect fatigue cracks of a certain minimum size, the morphology of the crack may be determined. The crack depth and gap width may be measured. The measurement of the crack gap may be determined, and the gap may vary along the depth and length of the crack. Thus, a protocol for crack gap measurement may be used. If the crack is formed due to stress and localized deformation, the crack gap is expected to change smoothly along the crack depth and/or length. If there are abrupt changes in the crack gap, indicating missing material, it may be due to crack specimen surface preparation process. Missing material areas may be avoided in the crack gap measurement. Statistical quantities such as mean and standard deviation of measurements along the crack depth (or expected x-ray direction) may be used.

Once the crack depth and gap are known, the image quality indicator may be selected by choosing a classification with interface gap less than or equal to the crack gap width. Additional description of the image quality indicator system 100 is provided below.

Crack IQI Qualification

Based on the HPP interface gap class, the HPP may qualify to be part of the appropriate crack IQI to verify detection of crack of certain depth and gap. The crack IQI may be qualified for the given application. Here, the chosen crack IQI provides a comparable x-ray image signature to that of relevant cracks. The signature may be compared visually for film radiography, but for digital radiography, the comparison may be based on a measurement of indication width and contrast, and/or contrast-to-noise ratio. The HPP may provide a circular indication of the hole-plug interface for low incident angle x-rays. For oblique angle x-rays, the hole-plug interface indication may be in segments of a circle. The hole-plug interface provides crack orientation clocking from 0 to 360°. Relevant portions of the HPP interface indication may be detected. Due to circular gap interface, there are two opposing locations with the same clock orientations that are spaced apart by the plug diameter. Therefore, farthest location of the detected HPP interface indication may be noted to determine the limit x-ray angle. This is illustrated in FIG. 11 and FIG. 12.

It may be assumed that the x-ray set-up on the crack specimen and the crack IQI are identical and similar to the actual part inspection. The material, part thickness, and a/t ratio may be comparable between the crack specimens and crack IQIs, but may not be exact. The limit angle for crack detection may be the same or higher than the limit angle for crack IQI detection in this comparison. The crack IQI qualification may be performed for low and high part thicknesses, and there may be some minimum number of cracks (e.g., six cracks) used to address variability in the detectability of real cracks.

The IQI may be qualified for a particular application if results of the qualification study indicate that the crack IQI can provide x-ray indication comparable to x-ray indications of real cracks. The use of crack IQI may provide an x-ray crack detection technique. One objective of crack IQI is to verify the crack detectability simultaneously with x-ray inspection similar to NDE technique standardization, which may be performed before beginning the NDE procedure on the part and similar to verification of maintaining standardization which is performed after completing the NDE procedure on the part.

HPP Design Considerations

The HPP interface indication quality may be uniform. In one embodiment, if the HPP is rotated (e.g., by 90°), and x-ray imaged again in the exact same location, the two x-ray indications may be identical. In other words, the interface gap indication may look identical with rotational symmetry. The nature of gap may be different between crack faces and the HPP interface. Some cracks, termed as tight cracks, may have intermittent contact. Also, compressive stress can close the crack or reduce the crack gap and increase the area of contact between the crack faces. Thus, the crack gaps may have no contact between crack faces, or may have partial contact between the crack faces. Other than custom interface gaps, the HPP design may assume an interference fit with intermittent contact in the interface, and therefore, the HPP has partial interface gaps. Custom interface gaps may be designed as intermittent or non-contact. The gap can be measured on the image of the crack or HPP interface using image processing software. If the crack or HPP interface is oriented vertically in the image, then the gap can be measured at every horizontal pixel line that intersects the vertical indication. Such measurement may result in a distribution of gap measurements providing mean and standard deviation. Since cracks may or may not have intermittent contact, the standard deviation of the crack gap measurement may be smaller than the HPP interface gap for the same average gap. Therefore, the HPP with the lower average interface gap with comparable standard deviation of gap may be qualified for verifying detection of cracks. As a result, the standard deviation of the interface gap may be set as low as possible in the HPPs.

This may be accomplished by controlled manufacturing processes. Straightness and roundness of the shaft and pipe bore are relevant parameters. Therefore, there may not be any hand polishing or machining using regular machine shop tools. The machining and finishing of the shaft outer diameter surface and the pipe bore surface may be accomplished using precision machine tools providing dimensional accuracy to 0.0001". The surface finish for both the shaft and the bore are relevant parameters. Abrasive type (e.g., grinding and honing) of metal finishing operation may be used for finer classes of interface gaps. The surface finish for both of the parts may be comparable. The sum of the two finishes can be considered to be upper bound for the interface gap due to contribution to interface gap from other factors given in the following relationship.

$$W(\mu,\sigma) \to f_3(\delta_0(Ra_{bore}+Ra_{shaft}),\Delta_r,\Delta_s) \qquad \text{(equation 4)}$$

where, W=gap described as distribution defined by mean $\mu$ and standard deviation $\sigma$,
$Ra_{bore}$=surface finish of bore in micro inches,
$Ra_{shaft}$=surface finish of shaft in micro inches, $\delta_0$=diametrical interference or diametrical gap,
$\Delta_r$=out of roundness,
$\Delta_s$=out of straightness, and
$f_3$=function.

The measured interface gap distribution mean and standard deviation may depend upon diametrical interference, surface finishes of the bore and shaft, straightness of bore and shaft, roundness of bore and shaft, or a combination thereof. Moreover, clocking of the shaft in bore also can provide variability in the interface gap. The shaft may be assembled in the bore in a frictionless manner to avoid rubbing between mating surfaces, and surface smearing, which can also generate particulates that may get trapped in the interface increasing the interface gap. The shaft insertion end may be tapered with rounded corners, and the bore opening receiving the shaft may have a fillet radius. FIG. 24 shows the HPP interface section images under a microscope and provides example of discrete interface gap measurements that are part of the interface gap distribution.

One method to achieve a frictionless assembly of the shaft in the pipe is to have a temperature difference between the two parts. The shaft can be cooled to shrink its diameter while the pipe is kept at room temperature such that its diameter remains substantially constant. This assembly may be performed quickly once the shaft enters the pipe bore. As heat from the pipe transfers to the shaft, the temperature may equalize, causing interference pressure, which may prevent further frictionless movement of the shaft in the pipe. Another technique is to raise the temperature of the pipe and keep the shaft at room temperature. This may be done if rising temperature does not change the heat temper and affect x-ray image. The minimum temperature difference to shrink the shaft by $2\delta\_0$ or increase diameter of the bore by $2\delta\_(0)$ is given by:

$$\Delta T_{min} = \frac{\delta_0}{R_2 \alpha_L} \quad \text{(equation 5)}$$

where, $R_2$=radius of shaft or bore, and
$\alpha_L$=coefficient of linear thermal expansion.

The diametrical interference results in interference pressure. The pressure may be useful for stabilizing the assembly, but can be an issue for a very thin HPP, as it might cause the plug and/or the washer to buckle and cause out of plane movement possibly during the slicing operation, and later during the finishing operations. Normal handling forces may cause the plug to pop out of the hole. Therefore, resin mounting (encasing) may be useful for slicing very thin HPPs. The resin encasing may be left as-is after manufacturing, as its effect on x-ray imaging may be tolerable due to its lower density. FIG. 22 shows examples of the resin-mounted HPP. The interference pressure P is given by equation 6:

$$P = \frac{\delta_0}{r_2 \left( \frac{r_2^2(-1+v)}{E(-r_1^2+r_2^2)} + \frac{r_1^2(1+v)}{E(r_1^2-r_2^2)} - \frac{(-1+v)}{E} \right)} \quad \text{(equation 6)}$$

where, $v$=Poisson's ratio,
$E$=Young's modulus, and
$r_1, r_2$=radius of pipe and interface radius respectively.

FIG. 20 shows graphics for radii. The buckling force may be calculated. As a simple check, the plug may be modeled as a square with each side having the same as the diameter as the plug. The buckling stress may be calculated for a simple column in pinned-pinned end conditions. The buckling stress for the square column may be assumed to be smaller than that required for bucking the round plug with uniformly distributed radial pressure. The buckling compressive stress Pb can be calculated using following equations:

$$I = \frac{bh^3}{12} \quad \text{(equation 7)}$$

$$P_b = \frac{\pi^2 EI}{bhL^2} \quad \text{(equation 8)}$$

where, b=width of square column,
L=height of square column, and
h=thickness of the square column.

In one embodiment, $b=L=2r_2$ and $h=a$. High buckling stress may be desired in comparison to the interference pressure for smallest thickness HPP. The smallest thickness may be about 0.030". Dry ice (solid $CO_2$) may provide a cooling change in temperature from room temperature of ~105 K. Liquid nitrogen ($LN_2$) may provide a cooling change in temperature from room temperature of ~220 K. Using these cooling effects, the nominal shaft diameter of 0.5", pipe outer diameter of 1", and radial interference of 0.00025", the following calculations were performed using above equations for four different materials.

TABLE 2

Example of design calculations

| Material | Coefficient of Thermal Expansion,/K $\alpha_L$ | Young's Modulus, psi E | Poisson's ratio v | Radial Interference, in $\delta_0$ | Interference Pressure, psi P | Minimum Temperature Difference for Assembly, K $\Delta T_{min}$ | Square side, in b, L | Thickness, in h | Square plate buckling stress, psi $P_b$ | Shaft Cooled for Assembly | Pipe Warmed up ~20K |
|---|---|---|---|---|---|---|---|---|---|---|---|
| Al-6061 | 1.58E−05 | 1.00E+07 | 0.33 | 0.00025 | 3,750 | 63 | 0.5 | 0.03 | 29,609 | Dry ice | No |
| Ti-6Al-4V | 5.29E−06 | 1.55E+07 | 0.34 | 0.00025 | 5,812 | 189 | 0.5 | 0.03 | 45,894 | LN2 | No |
| CRES 304 | 1.09E−05 | 2.83E+07 | 0.29 | 0.00025 | 10,613 | 92 | 0.5 | 0.03 | 83,793 | Dry ice | Yes |
| Inconel 718 | 8.54E−06 | 2.60E+07 | 0.28 | 0.00025 | 9,750 | 117 | 0.5 | 0.033 | 76,983 | Dry ice | Yes |

The above calculations show that for the chosen design parameters, the buckling stress is about 7.9 times the inference pressure and is considered to be not an issue to cause buckling, but a resin encasing may be used for a thinner HPP. The temperature difference for assembly also indicates the choice of dry ice or liquid nitrogen. Additional temperature difference may be obtained by warming the pipe by about 20 K. To create the desired interface gap class, the surface finish for the shaft and bore may be determined by trial and error. In general, if the surface finish number is increased, a higher interface gap is expected. The finest surface finish may help to obtain lowest interface gap.

In conclusion, HPPs and shims stacked together make the crack IQI. The crack IQI provides simulated cracks in material and geometry that are similar to the actual part. The crack IQI may be used in an x-ray inspection set-up that is similar the part inspection set-up. If a qualified crack IQI is available at the time of part inspection, the x-ray technique sensitivity for crack detection can be verified for the inspection set-up. The cost of manufacturing the HPPs is likely to be at least an order of magnitude cheaper than making fatigue crack specimens in different thicknesses. Therefore, inexpensive crack IQIs can be manufactured covering detection of various types of cracklike flaws using various interface gap classes. Also, once crack IQI qualification testing validates correlation of crack IQI interface gap measurements with real crack gap measurements for a range of crack gaps, any x-ray application that falls within the range of the crack gaps may be covered by the qualification.

What is claimed is:

1. An image quality indicator (IQI) system, comprising:
a crack IQI comprising:
a penetrameter having a first body and a second body disposed in the first body, wherein the first body has a first body inner surface defining a first body hole, and wherein the second body has a second body outer surface disposed adjacent the first body inner surface to form an interface having an interface gap that simulates a crack;
a radiation source spaced from the penetrameter and configured to transmit radiation rays to the penetrameter; and
a radiation detector disposed adjacent the penetrameter and configured to generate an IQI radiographic image indicative of an interface gap characteristic of the interface gap.

2. The IQI system of claim 1, wherein the crack IQI further includes a shim, and wherein the penetrameter and the shim are stacked together.

3. The IQI system of claim 1, wherein the first body comprises a washer and the second body comprises a plug, wherein the washer and the plug have an interference fit where the first body inner surface abuts the second body outer surface.

4. The IQI system of claim 1, wherein the interface gap simulates a predetermined crack characteristic in a component part.

5. The IQI system of claim 4, wherein the predetermined crack characteristic is based on an interface gap width.

6. The IQI system of claim 5, wherein the penetrameter comprises a first penetrameter that is part of a penetrameter set, wherein the penetrameter set also comprises a second penetrameter, wherein the first penetrameter is classified in a first interface gap class having a first minimum interface gap and a first maximum interface gap, and the second penetrameter is classified in a second interface gap class having a second minimum interface gap and a second maximum interface gap, and wherein the first interface gap class is different than the second interface gap class.

7. The IQI system of claim 5, wherein the interface gap width is determined by taking a plurality of measurements that are substantially equally spaced along a length of the interface gap, averaging the measurements, and calculating a mean and a standard deviation of the measurements.

8. The IQI system of claim 1, wherein the interface includes a plurality of interface contact points, and wherein the interface gap includes a plurality of intermittent gaps defined by the plurality of interface contact points.

9. The IQI system of claim 1, wherein the first body and the second body form a top surface and a bottom surface, and wherein the penetrameter further comprises a resin mounting that at least partially encases at least one of the top surface and the bottom surface.

10. A method, comprising:
positioning a crack image quality indicator (IQI) adjacent to a radiation detector, wherein the crack IQI includes:
a penetrameter having a washer and a plug disposed in the washer, wherein the washer has a washer inner surface defining a washer hole, and wherein the plug has a plug outer surface disposed adjacent the washer inner surface to form a hole-plug interface having a predetermined interface gap configured to simulate a crack; and
radiographic imaging the penetrameter with a radiation source, the radiographic imaging comprising:
activating the radiation source; and
collecting a first radiographic image with the radiation detector.

11. The method of claim 10, wherein the penetrameter is classified in an interface gap class having a minimum interface gap and a maximum interface gap.

12. The method of claim 10, wherein the crack IQI is configured to simulate a component part, wherein the simulated crack is configured to simulate a crack in the component part, and wherein the simulated crack comprises a predetermined characteristic.

13. The method of claim 12, wherein the predetermined crack characteristic comprises an interface gap width.

14. The method of claim 12, further comprising determining that the first radiographic image displays the simulated crack.

15. The method of claim 14, further comprising:
positioning the component part adjacent to the radiation detector;
radiographic imaging the component part with the radiation source, the radiographic imaging comprising:
activating the radiation source; and
collecting a second radiographic image with the radiation detector; and
determining that the second radiographic image displays the crack.

16. A method for detecting cracks, comprising:
increasing a temperature differential between a shaft and a pipe to allow a frictionless assembly of the shaft into the pipe to form a pipe-shaft assembly, wherein the shaft, the pipe, or both are metallic;
equalizing temperatures of the shaft and the pipe to form an interference fit between the shaft and the pipe in the pipe-shaft assembly;
cutting the pipe-shaft assembly into a plurality of sections, wherein each section serves as at least a portion of a crack image quality indicator (IQI), and wherein each crack IQI comprises:

a washer that is part of the pipe, wherein the washer has a washer inner surface defining a washer hole; and a plug that is part of the shaft, wherein the plug has a plug outer surface disposed adjacent the washer inner surface to form a hole-plug interface having an interface gap;

positioning a first of the crack IQIs at least partially between a radiation source and a radiation detector, wherein a central longitudinal axis through the first crack IQI is substantially perpendicular to the radiation detector;

positioning a shim at least partially between the first crack IQI and the radiation detector;

performing a qualification test using an IQI physical set-up, wherein the qualification test comprises:

radiographic imaging the first crack IQI with the radiation source, wherein the radiographic imaging comprises:

activating the radiation source which emits a normal ray and a limit ray, wherein the normal ray is substantially perpendicular to the radiation detector, wherein the limit ray is non-perpendicular to the radiation detector, wherein the normal ray, the limit ray, or both pass through the first crack IQI and are received by the radiation detector, and wherein an angle between the normal ray and the limit ray at least partially defines a coverage length on the radiation detector; and collecting a first radiographic image with the radiation detector in response to receiving the normal ray, the first ray, or both; and detecting a simulated crack in the first IQI based at least partially upon the first radiographic image, wherein the simulated crack is detected at least partially within the coverage length.

17. The method of claim 16, further comprising:

performing an inspection test on a component part after detecting the simulated crack in the first IQI, wherein the inspection test is performed using an inspection physical set-up that is based upon the IQI physical set-up, wherein the inspection test is non-destructive, and wherein the inspection test comprises:

radiographic imaging the component part with the radiation source, wherein the component part is metallic, and wherein the radiographic imaging comprises:

activating the radiation source which again emits the normal ray and the limit ray, wherein the normal ray, the limit ray, or both pass through the component part and are received by the radiation detector; and collecting a second radiographic image with the radiation detector in response to receiving the normal ray, the limit ray, or both; and determining whether a crack exists within the coverage length in the component part based at least partially upon the second radiographic image.

18. The method of claim 17, wherein a thickness of the first IQI plus a thickness of the shim is substantially equivalent to a thickness of the component part.

19. The method of claim 17, wherein:

a distance between the radiation source and the first crack IQI in the IQI physical set-up is substantially the same as a distance between the radiation source and the component part in the inspection physical set-up, an angle of the limit ray is substantially the same in the IQI physical set-up and the inspection physical set-up, an energy level is substantially the same in the IQI physical set-up and the inspection physical set-up, an exposure is substantially the same in the IQI physical set-up and the inspection physical set-up, and a collimation is substantially the same in the IQI physical set-up and the inspection physical set-up.

20. The method of claim 16, further comprising positioning a second shim at least partially between the simulated crack IQI and the radiation source prior to performing the qualification test, wherein the simulated crack IQI is positioned at least partially between the shim and the second shim.

\* \* \* \* \*